United States Patent [19]
Surratt et al.

[11] Patent Number: 5,688,256
[45] Date of Patent: Nov. 18, 1997

[54] EVACUATION UNIT AND METHOD FOR CONTROLLING THE RELEASE OF GAS FROM A BODY CAVITY FOLLOWING SURGERY

[75] Inventors: W. Farris Surratt, Lawndale; Steven K. Brockman, Shelby, both of N.C.

[73] Assignee: Lap-Cap Associates, Shelby, N.C.

[21] Appl. No.: 515,623

[22] Filed: Aug. 16, 1995

Related U.S. Application Data

[63] Continuation of Ser. No. 205,622, Mar. 3, 1994, abandoned.

[51] Int. Cl.$^6$ .............. A61F 5/44; A61M 1/00; A61M 31/00
[52] U.S. Cl. .............. 604/355; 604/19; 604/23; 604/275; 604/327; 604/328; 604/333
[58] Field of Search .............. 604/19, 21, 23, 604/26, 28–30, 32, 45, 129, 355, 275–277, 317–319, 324, 327, 328, 333; 128/4

[56] References Cited

U.S. PATENT DOCUMENTS

| | | | |
|---|---|---|---|
| 4,735,603 | 4/1988 | Goodson et al. | 604/26 |
| 4,787,894 | 11/1988 | Turnbull | 604/319 |
| 4,813,931 | 3/1989 | Hauze | 604/319 |
| 4,930,997 | 6/1990 | Bennett | 604/319 |
| 4,936,318 | 6/1990 | Schoolman . | |
| 4,957,492 | 9/1990 | McVay | 604/319 |
| 5,002,534 | 3/1991 | Rosenblatt | 604/317 |
| 5,047,010 | 9/1991 | Ams et al. . | |
| 5,098,375 | 3/1992 | Baier . | |
| 5,127,411 | 7/1992 | Schoolman et al. . | |
| 5,249,579 | 10/1993 | Hobbs et al. . | |
| 5,360,396 | 11/1994 | Chan | 604/26 |

OTHER PUBLICATIONS

"Holding Back Electrosurgical Plume and Aerosolized Sprayback Limits Risk of Viral Infection in Endoscopic Procedures", Full Scope, vol. 1, Issue 1, 1993, published by Ethicon Endo–Surgery.

Primary Examiner—John G. Weiss
Assistant Examiner—Dennis Ruhl
Attorney, Agent, or Firm—Bell, Seltzer, Park & Gibson, P.A.

[57] ABSTRACT

An evacuation unit and method for using the unit for controlling the release from a body cavity of aerosolized blood and other body fluids or other contaminants contained in the gas present in the body cavity during an endoscopic surgical procedure is disclosed. The unit includes a port in fluid communication with the body cavity through which the contaminated gas passes to an evacuation connector having a first end in fluid communication with the port and a second end and an aerosol trap in fluid communication with the second end of the evacuation connector such that the aerosol-containing gas is able to flow from the connector through the aerosol trap whereby the aerosolized fluids or other contaminants in the gas are prevented from entering the atmosphere of the operating room. The connector preferably has a flow control valve between the ends.

3 Claims, 1 Drawing Sheet

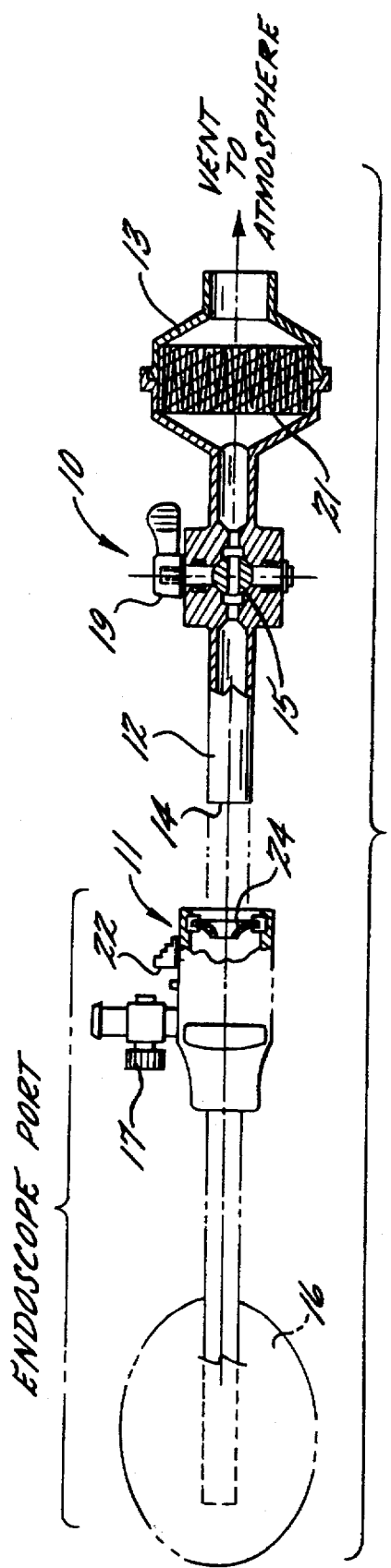
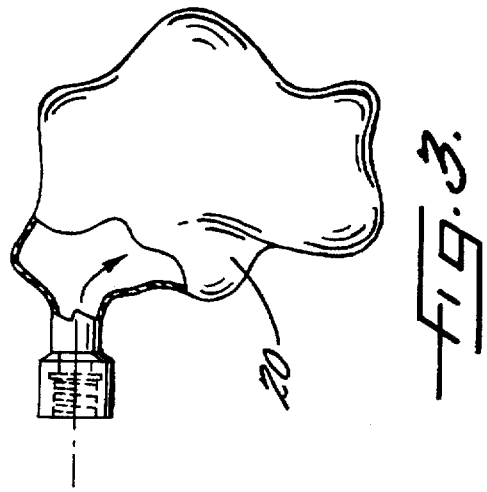
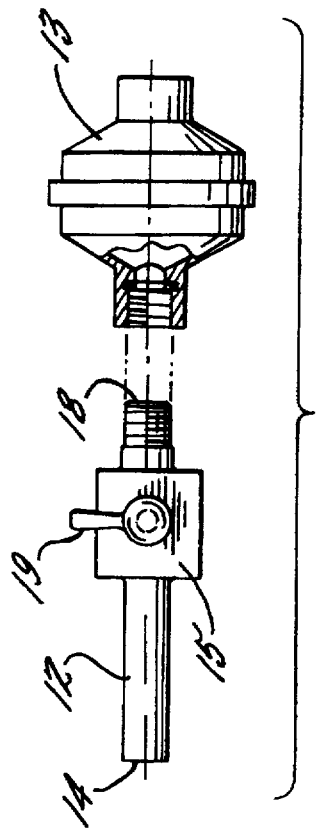

though the gas, and then removes contaminants from the gas.

EVACUATION UNIT AND METHOD FOR CONTROLLING THE RELEASE OF GAS FROM A BODY CAVITY FOLLOWING SURGERY

This application is a continuation of application Ser. No. 08/205,622, filed Mar. 3, 1994 now abandoned.

BACKGROUND OF THE INVENTION

1. Field of the Invention

The present invention relates to an evacuation unit for controlling the release of carbon dioxide or other gas from a body cavity following a surgical procedure and to a method for using the evacuation unit. More specifically, the present invention relates to an evacuation unit for use following an endoscopic procedure. This unit is used to contain aerosol particles and other contaminants present in the carbon dioxide or other gas expelled from a body cavity. The present invention also relates to a method for using the evacuation unit.

2. Description of the Prior Art

Endoscopic surgical procedures are commonly used to treat a number of problems. In the procedure, an access port is introduced through the wall of the body cavity. In some procedures carbon dioxide gas is insufflated to distend the walls of the cavity (the abdomen, for example). In other procedures, air is allowed to enter the body cavity (the chest, for example). At the conclusion of the surgical procedure the gas is allowed to escape from the cavity into the atmosphere of the operating room. Blood, body fluids, or other contaminants can be present in this gas exiting from the body cavity in an aerosolized form. These contaminants can contain potentially infectious agents such as hepatitis and HIV viruses and the like. In addition, during procedures that employ a laser, combustion products (including smoke) are produced by the action of the laser on body tissues. These products can also be released into the atmosphere at the conclusion of the procedure.

When the surgical procedure is completed, it has been common practice to either allow gas within the body cavity to escape through the port or to remove the port and allow gas to escape through the wound created by insertion of the port. This gas (containing noxious and potentially infectious materials) enters the atmosphere without treatment or cleansing. It is, of course, desirable and necessary to protect operating room personnel against exposure to this kind of hazardous material.

SUMMARY OF THE INVENTION

It is accordingly an object of the present invention to provide equipment to allow the escape of gas from a body cavity without contamination of the operating room.

Another object of the present invention is to provide a containment unit for controlling the escape of blood and other body fluids in aerosol form in the gas escaping from a body cavity into the operating room.

Still another object of this invention is to provide for waste gas removal following an endoscopic surgical procedure.

It is yet another object of the present invention to provide a method for removing blood and other body fluids contained in aerosol form and any other undesirable material from the gas expelled from the body cavity following an endoscopic surgical procedure.

The objects of this invention are accomplished by providing an evacuation unit for insertion into the outlet end of a port, such as the one used during a surgical procedure, in fluid communication with a body cavity filled with gas containing aerosolized blood or body fluids or other contaminants. The unit includes an evacuation connector in fluid communication with the port. A flow control valve is positioned in the evacuation connector between the ends thereof. The outlet side of the evacuation connector is in fluid communication with an aerosol trap. In one embodiment of the evacuation unit the aerosol trap is a filter which removes aerosolized particles and other contaminants and allows the cleansed gas to pass to the atmosphere. In an alternative embodiment, the aerosol trap is a collection bag that is placed in fluid communication with the evacuation connector and which collects the gas and contaminants for proper disposal.

In accordance with the method of this invention, removal of blood and body fluids in aerosolized form and other contaminants from the gas introduced into a body cavity includes the steps of: passing the gas containing contaminants from a body cavity through the evacuation connector; controlling the flow of the aerosolized particles and contaminants containing gas through the evacuation connector to an aerosol trap; and removing the aerosolized fluids and contaminants from the gas.

The advantage of using the evacuation unit of the present invention is that the evacuation unit is simple and easy to use, is effective to remove the contaminants from the gas and may be inexpensively made and used only once.

BRIEF DESCRIPTION OF THE DRAWINGS

The foregoing objects, features, advantages and preferred embodiments of the evacuation unit and method of the present invention will be better understood from the following detailed description taken in conjunction with the accompanying drawings in which:

FIG. 1 illustrates an embodiment of this invention showing a patient body cavity with a port inserted into the site of the surgical procedure and a partial section of the evacuation connector and filter;

FIG. 2 is a top view illustrating another embodiment of the evacuation connector and filter of the present invention; and FIG. 3 illustrates another embodiment of the evacuation unit of the present invention illustrating a collection bag.

DETAILED DESCRIPTION OF THE PREFERRED EMBODIMENTS

Referring more specifically to the drawings, there is shown in FIG. 1 an embodiment of the evacuation unit 10 for controlling the escape of gas from a body cavity 16 embodying the features of the present invention. As illustrated, there is an endoscope port 11 inserted into the body cavity of the patient and used during the surgical procedure. When the procedure is completed, an evacuation connector 12 connected to an aerosol trap, shown as a filter 13, is inserted in fluid communication into the outlet end of the port 11.

The port 11 may be any one of a variety of standard available surgical instruments, such as a trocar. As shown in FIG. 1, the port 11 is inserted through an incision into a body cavity 16. Gas may be insufflated through control valve 17 to distend the walls of the body cavity. The outlet end of the port 11 when not in use may be sealed by an internal closure (not shown) which is controlled by desufflate handle 22. When instruments are inserted into the outer end of port 11 a sealing fit is maintained by flexible ring fitting 24.

The evacuation connector 12 is preferably a tube-like member having a first end 14 sized to fit in fluid communication with the outlet end of port 11. The evacuation connector 12 is preferably made of a low cost plastic material which should be disposed of upon completion of the surgical procedure. The evacuation connector 12 preferably has a flow control valve 15 controlled by handle 19 which regulates the rate of discharge.

In the embodiment illustrated in FIGS. 1 and 2, the aerosol trap 13 is in fluid communication with the rear or outlet end 18 of evacuation connector 12 and has a filter 21 therein. In the embodiment of FIG. 1, the evacuation connector 12 and the filter-containing aerosol trap 13 are shown as a single unit. The aerosol trap 13 contains a filter medium 21 of a suitable pore size to trap aerosolized particles. Suitable filter mediums include those of polypropylene fiber mesh and cellulose. One such polypropylene filter medium is sold under the name Filtrete® and is available from 3M. In the embodiment shown in FIG. 2, the connector and filter are shown as separate units which may be easily joined such as by screwing together. As used herein, an aerosol is a suspension in a gas of microscopic liquid or solid particles, such as smoke, dust, fog or smog, that tend to remain dispersed rather than to settle. True aerosol particles generally range from $10^{-7}$ to $10^{-4}$ cm in diameter.

The embodiment shown in FIG. 3 is yet another form of this invention wherein a collection bag 20 is placed in fluid communication with the outlet end 18 of evacuation connector 12. The gas escaping from the body cavity is collected in the bag and disposed of properly.

It should be understood that the evacuation unit 10 is a single use unit which is replaced with each surgical procedure.

In operation, a port 11 is introduced into a body cavity 16, e.g., the abdomen, through an incision. The body cavity may be distended by a flow of gas through the port. When a desired pressure or volume is reached, the flow of gas into the body cavity is stopped. The endoscopic procedure is then performed. If leakage around the port and tissue occurs additional gas may be added to body cavity to maintain the desired pressure or volume during the procedure. Following the procedure, the surgical instruments, e.g., laser or the like, are withdrawn from the endoscope port 11 and before substantial amounts of gas escape the connector 12, with the flow valve in shut off position is inserted into the rear of the port. The filter is either preattached to the connector or may be added at that time. The flow valve is then opened and gas from the body cavity is allowed to pass through the filter where the blood and other particles are held on the filter medium and the clean gas is allowed to pass to the atmosphere of the operating room. The filter may then be disposed of properly so that there is no contamination of the operating room personnel. In the alternative embodiment a collection bag is used to collect both the gas and aerosolized blood and body fluids and other contaminants. The bag is subsequently disposed of in the proper manner.

In the figures and specification, there have been disclosed preferred embodiments of the invention. While specific terms are employed, they are used in a generic and descriptive sense only, and not for the purpose of limiting the scope of the invention being set forth in the following claims.

What is claimed is:

1. In a method following an endoscope procedure for controlling the escape of an aerosol-containing gas that is under pressure from a body cavity into the air of an operating room, wherein an access port having a first end, an outer end and a flow valve has been placed through an incision in said body cavity during said procedure, the improvement comprising:

closing said flow valve of said access port;

inserting an evacuation connector into said outer end of said access port;

opening the flow valve of said access port to allow said aerosol-containing gas under pressure having aerosolized blood and body fluids or other contaminants present in a body cavity contained therein to pass from said body cavity through said access port and into said evacuation connector;

controlling the flow of said aerosol-containing gas through said evacuation connector and then through a filter;

filtering said aerosolized blood and body fluids or other contaminants from said aerosol-containing gas to obtain a clean gas; and thereafter expelling said clean gas.

2. An evacuation system for removing gas present in a body cavity during a surgical procedure and cleansing blood and body fluids in aerosolized form and other contaminants from the removed gas comprising in combination:

a trocar having a first end adapted for fluid communication with said body cavity, and an outer end;

an evacuation connector having a first end adapted for insertion into said outer end of said trocar, a second end, and a flow control valve located between said first end and said second end, said outer end of said trocar having a flexible ring fitting for forming a sealing relationship with said evacuation connector; and an aerosol trap having a first end in direct communication with said second end of said evacuation connector, an outlet end of said aerosol trap for gas exiting said evacuation unit, and a filter located between said first end and said outlet end, said filter having a pore size to trap aerosolized particles in said gas.

3. The evacuation system according to claim 2 wherein said second end of said evacuation connector and said first end of said aerosol trap are formed together as a single unit.

* * * * *